United States Patent
Terwey

(10) Patent No.: US 9,192,364 B2
(45) Date of Patent: Nov. 24, 2015

(54) VASCULAR CLOSURE DEVICE WITH PUSH/PULL COMPACTION SYSTEM AND METHODS

(71) Applicant: St. Jude Medical Puerto Rico LLC, Caguas, PR (US)

(72) Inventor: Russell D. Terwey, St. Michael, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 198 days.

(21) Appl. No.: 13/757,001

(22) Filed: Feb. 1, 2013

(65) Prior Publication Data
US 2014/0222063 A1    Aug. 7, 2014

(51) Int. Cl.
  *A61B 17/08*    (2006.01)
  *A61B 17/00*    (2006.01)

(52) U.S. Cl.
  CPC ... *A61B 17/0057* (2013.01); *A61B 2017/00623* (2013.01); *A61B 2017/00654* (2013.01); *A61B 2017/00659* (2013.01)

(58) Field of Classification Search
  CPC .............. A61B 17/0057; A61B 2017/00637; A61B 2017/00654; A61B 2017/00659; A61B 2017/00623
  USPC ................... 606/213, 215, 216, 232
  See application file for complete search history.

(56) References Cited

U.S. PATENT DOCUMENTS

2010/0286727 A1* 11/2010 Terwey .................. 606/213

* cited by examiner

*Primary Examiner* — Ashley Fishback
(74) *Attorney, Agent, or Firm* — Holland & Hart

(57) ABSTRACT

A tissue puncture closure device includes an anchor, a suture connected to the anchor at a distal end of the suture, a sealing plug positioned proximal of the anchor, and a compaction assembly. The compaction assembly includes a compaction tube having a distal end and a proximal end, and a pivot arm having first and second ends and being rotatable about a pivot axis. The proximal end of the compaction tube is connected to the first end of the pivot arm and a proximal end of the suture is connected to the second end of the pivot arm. The compaction assembly also includes a release member operable to release the pivot arm to rotate between a first position wherein the compaction tube is withdrawn, and a second position wherein tension is applied in the suture and the compaction tube is advanced to compact the sealing plug.

20 Claims, 9 Drawing Sheets

VASCULAR CLOSURE DEVICE WITH PUSH/PULL COMPACTION SYSTEM AND METHODS

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., a catheter) may pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, may be stopped by utilizing vascular closure devices.

Typical closure devices place a sealing plug at the tissue puncture site. Deployment of the sealing plug may involve ejecting the sealing plug at a location in alignment with and adjacent to the tissue puncture along an outer surface of the vessel and within a percutaneous tissue tract. A challenge related to such deployment involves locating the tissue puncture in order to properly place the sealing plug in a position that provides sealing of the tissue puncture. Another challenge relates to deploying and compacting the sealing plug without advancing the sealing plug through the tissue puncture into the vessel. Opportunities exist for improvements in this technical area.

SUMMARY

One aspect of the present disclosure relates to a tissue puncture closure device that includes an anchor, a suture connected to the anchor at a distal end of the suture, a sealing plug slidingly mounted to the suture and positioned proximal of the anchor, and a compaction assembly. The compaction assembly includes a compaction tube, a pivot arm and a release member. The compaction tube has a distal end and a proximal end. The pivot arm includes first and second ends and is rotatable about a pivot axis. The proximal end of the compaction tube is connected to the first end of the pivot arm and a proximal end of the suture is connected to the second end of the pivot arm. The release member is operable to release the pivot arm to rotate between a first position wherein the compaction tube is withdrawn, and a second position wherein tension is applied in the suture and the compaction tube is advanced to compact the sealing plug.

The compaction assembly may provide a 1:1 ratio of longitudinal movement of the compaction tube and suture when the pivot arm rotates. The compaction assembly may include a biasing member operable to bias the pivot arm toward the second position. The tissue puncture closure device may further include a housing, and the pivot arm is positioned in the housing. The compaction assembly may be slidable in a distal direction relative to the housing. The tissue puncture closure device may include a carrier tube, and the sealing plug is positioned in the carrier tube during insertion of the tissue puncture closure device into a puncture.

The carrier tube may retract relative to the sealing plug to expose the sealing plug at a location adjacent to the puncture. The pivot axis may be arranged perpendicular to a direction of motion of the compaction tube. The tissue puncture closure device may include a suture release operable to release tension in the suture after the sealing plug is compacted by the compaction tube. The compaction assembly may include a spool mounted to the second end of the pivot arm, the suture being wound about the spool. The release member may be manually operated upon withdrawal of the tissue puncture closure device from a tissue puncture.

Another aspect of the present disclosure relates to a tissue puncture closure device adapted for insertion into and sealing of a tissue puncture. The tissue puncture closure device includes a carrier tube, a sealing plug, an anchor, a suture connected to the anchor and extending through the carrier tube, a compaction member, and a pivot member. The pivot member includes first and second end portions, wherein the compaction member is coupled to the first end portion and the suture is coupled to the second end portion. Rotating the pivot member advances the compaction member to compact the sealing plug toward the anchor while applying tension in the suture.

The compaction member and suture may be coupled to the pivot member at locations equidistant from a rotation axis about which the pivot member rotates. The pivot member may include a rotation axis that is arranged perpendicular to a length dimension of the tissue puncture closure device. Pivoting the pivot member may move the compaction member between a withdrawn position and an advanced position. The suture and compaction member may be attached to opposite ends of the pivot member.

A further aspect of the present disclosure relates to a method of sealing a puncture in a wall of a vessel. The method includes providing a closure device having a sealing plug, an anchor, a compaction member, a suture connected to the anchor, and a pivot member. The method also includes inserting the closure device through the puncture to position the anchor within an interior of the vessel, withdrawing the closure device to contact the anchor against an interior surface of the vessel and deposit the sealing plug adjacent to an exterior surface of the vessel, and rotating the pivot member to apply tension in the suture and advance the compaction member to compact the sealing plug to seal the puncture.

The compaction member may be coupled to a first end portion of the pivot member and the suture may be coupled to a second end portion of the pivot member, and rotating the pivot member may include rotating the pivot member about a pivot axis. The method may include providing a carrier tube configured to house the sealing plug when inserting the closure device through the puncture, and ejecting the sealing plug from the carrier tube may occur before rotating the pivot member. The method may include providing a housing, the pivot member being positioned in the housing, and shifting the pivot member distally within the housing prior to rotating the pivot member.

Additional advantages and novel features will be set forth in the description which follows or may be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and are not intended to be limiting.

Throughout the drawings, identical reference numbers designate similar, but not necessarily identical, elements.

DETAILED DESCRIPTION

Figure 1:
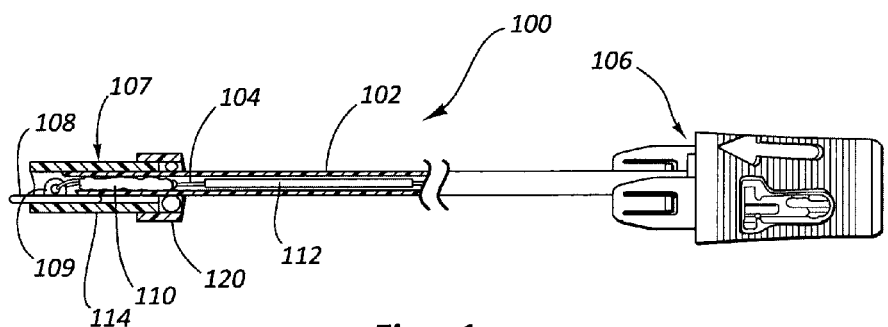
FIG. 1 is a side view of a tissue puncture closure device according to the prior art.

As mentioned above, vascular procedures are conducted throughout the world and require access to a vessel through a puncture. Most often, the vessel is a femoral artery. To close the puncture following completion of the procedure, many times a closure device is used to sandwich the puncture between an anchor and a sealing plug. However, sometimes the sealing plug is difficult to eject from the closure device and may not properly seat against an exterior situs of the arteriotomy. If the plug does not seat properly against the arteriotomy, there is a potential for prolonged bleeding. The present disclosure describes methods and apparatus that facilitate sealing plug ejection and proper placement of the sealing plug.

While the vascular instruments shown and described below include procedural sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

The present disclosure describes a medical device such as a tissue puncture closure device that is capable of retracting a procedural sheath relative to a closure device, exposing a distal end of the closure device prior to ejecting a sealing plug. The closure device drives the sealing plug toward a tissue puncture. The mechanism for driving the sealing plug may be selectably engagable and disengagable.

One aspect of the present disclosure relates to how the sealing plug of a tissue puncture closure device is compacted. The tissue puncture closure device may include a compaction assembly that is operable to apply tension force in the suture, which is attached at a distal end to an anchor that is positioned within the vessel, while concurrently advancing a compaction member (e.g., a compaction tube) that compacts the sealing plug toward the anchor to seal the vessel puncture. An example compaction assembly includes a rotating arm, which may also be referred to as a pivot member or pivot arm, which has the suture attached to one end of the rotating arm and the compaction member attached to an opposite end of the rotating arm. The rotating arm may be driven or rotated by a biasing member such a coil spring. The rotating arm is held in a first position in which the compaction member is held in a withdrawn position until the rotating arm is released, which allows the biasing member to rotate the rotating arm. As the rotating arm rotates, the compaction member is advanced to compact the sealing plug while tension is applied in the suture to hold the anchor firmly against an internal surface of the vessel. The anchor acts as a backstop against which the sealing plug is compacted to seal the vessel puncture.

The tissue puncture closure device may include a sliding mechanism such as a carriage that slides distally within a housing of the tissue puncture closure device. The compaction assembly may be mounted to the carriage. After positioning the anchor in the vessel, applying a withdrawal force to the housing shifts the carriage distally within the housing, thereby permitting the insertion sheath and carrier tube of the tissue puncture closure device to be withdrawn relative to the anchor and sealing plug to expose the sealing plug within a percutaneous incision adjacent to the vessel puncture. After exposing the sealing plug, the release member may be actuated to advance the compaction member to compact the sealing plug.

The tissue puncture closure device may also include a suture release that operates to release tension in the suture after compacting the sealing plug with the compaction member. In one example, the suture release releases a spool about which a proximal end of the suture is wound, wherein the spool is attached to one end of the pivot member. In another example, the suture release operates to release the biasing forces being applied by the biasing member to the rotating arm.

Referring now to the drawings, and in particular to FIGS. 1-4, a vascular puncture closure device 100 is shown according to the prior art. The vascular puncture closure device 100 includes a carrier tube 102 with a suture or filament 104 extending at least partially therethrough. The vascular puncture closure device 100 also includes a first or proximal end 106 and a second or distal end 107. External to the distal end 107 of the carrier tube 102 is an anchor 108. The anchor may be an elongated, generally stiff, low profile member including an eye 109 formed at the middle. The anchor 108 is typically made of a biologically resorbable polymer.

The filament 104 is threaded through the anchor 108 and back to a collagen plug 110. The collagen plug 110 may be comprised of, for example, randomly oriented fibrous material bound together by chemical means. The collagen plug 110 is slidingly attached to the filament 104 as the filament passes distally through the carrier tube 102. As the filament traverses the anchor 108 and reenters the carrier tube 102, the filament 104 is securely slip knotted proximal to the collagen plug 110 to facilitate cinching of the collagen plug 110 when the vascular puncture closure device 100 is properly placed and the anchor 108 deployed (see FIG. 4).

The carrier tube 102 typically includes a compaction member 112 disposed therein. The compaction member 112 is slidingly mounted on the filament 104 and may be used by an operator to compact the collagen plug 110 toward the anchor 108 at an appropriate time to seal a vascular puncture 118 within a percutaneous incision 119.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102 (see FIG. 1). The flush arrangement of the anchor 108 and carrier tube 102 allows the anchor 108 to be inserted into a procedure sheath such as insertion sheath 116 as shown in FIGS. 2-4, and eventually through an vascular puncture 118.

Figure 2:
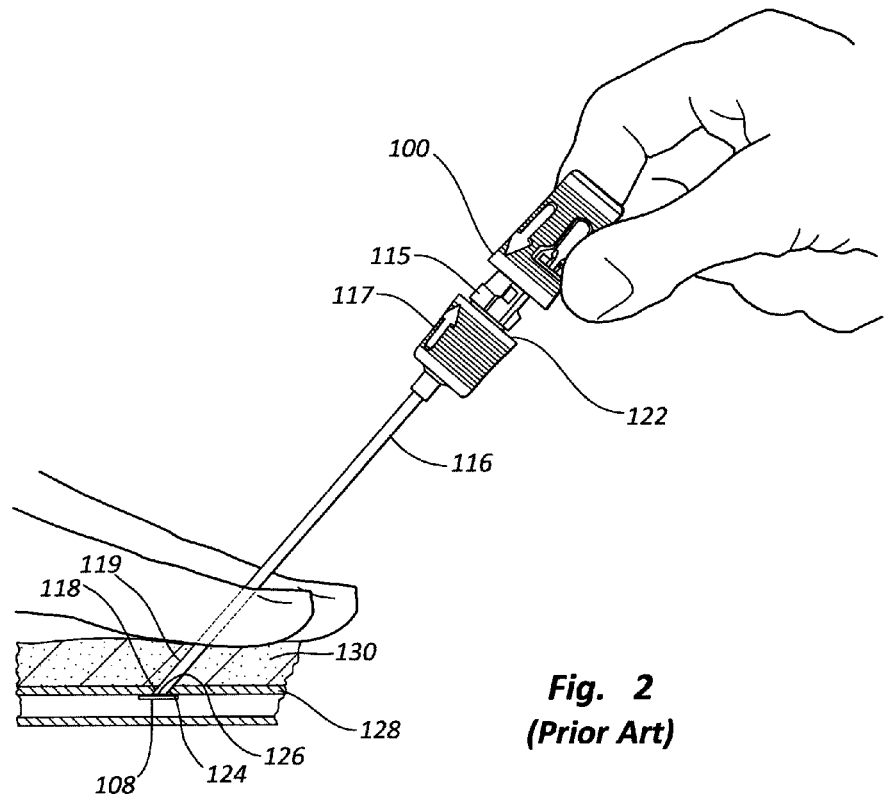
FIG. 2 is a side view of the tissue puncture closure device of FIG. 1 inserted into an insertion sheath and engaged with a vessel.
Figure 3:
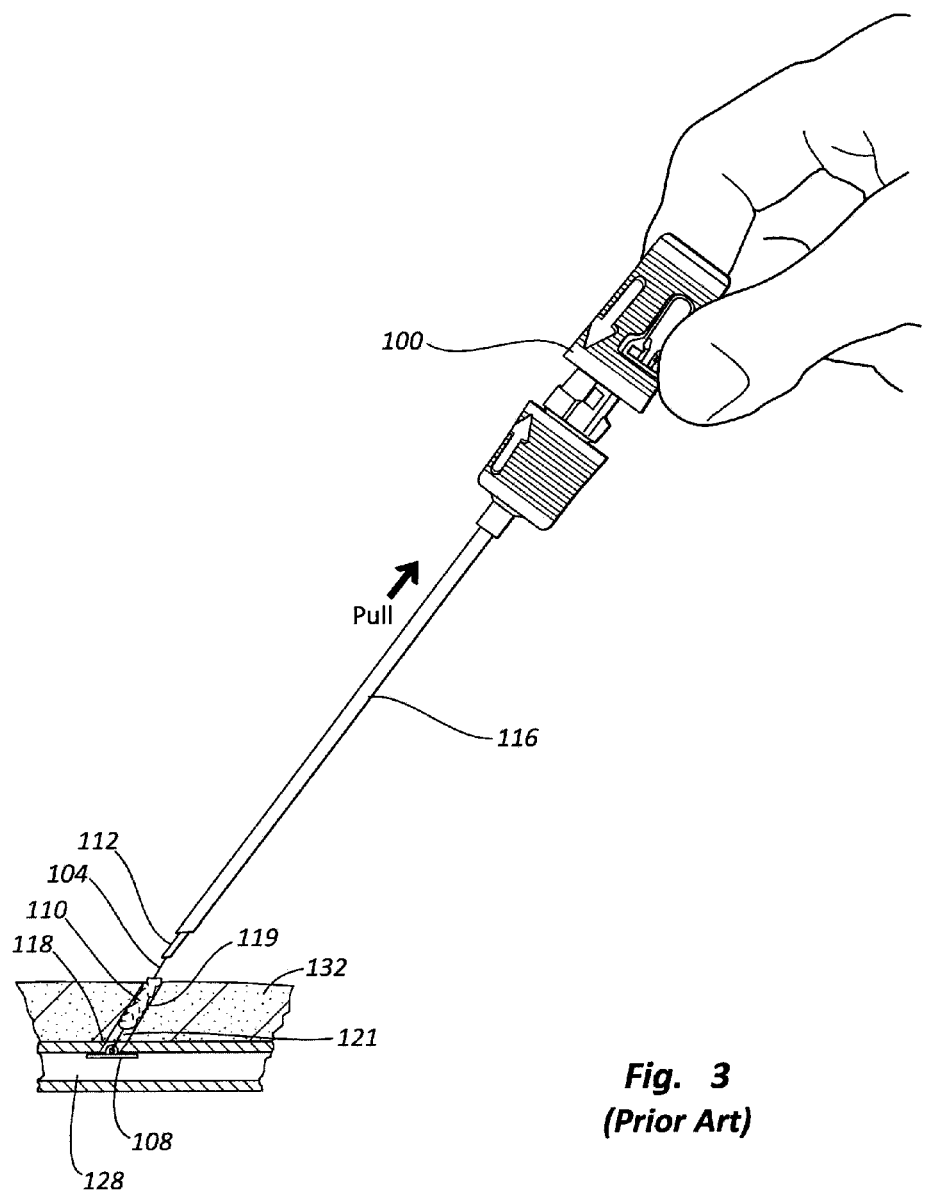
FIG. 3 is a side view of the tissue puncture closure device and an insertion sheath being withdrawn from a vessel to deploy a sealing plug.
Figure 4:
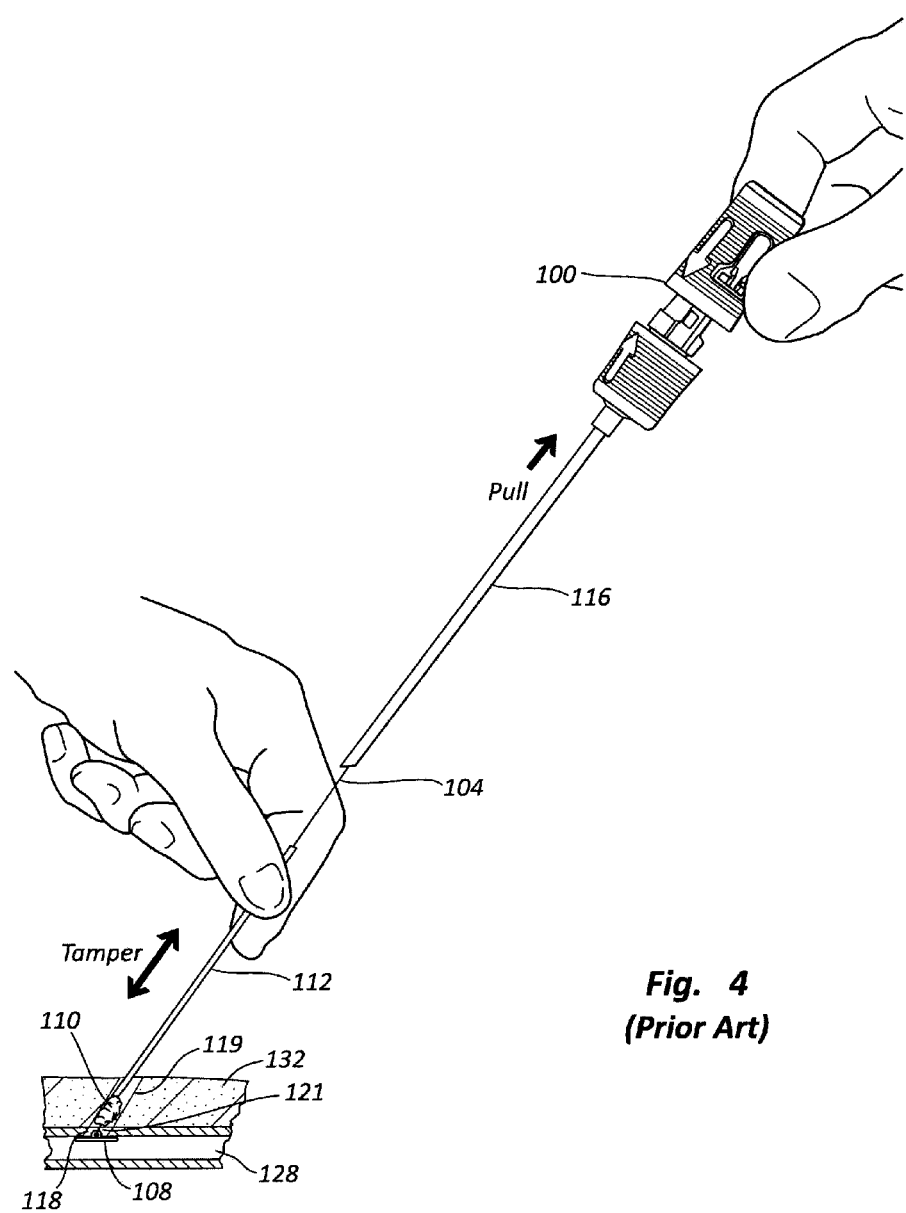
FIG. 4 is a side view of the tissue puncture closure device of FIG. 1 showing manual compaction of the sealing plug.

The insertion sheath 116 is shown in FIGS. 2-4 inserted through a percutaneous incision 119 and into an artery 128. The bypass tube 114 (see FIG. 1) may include an oversized head 120 that prevents the bypass tube 114 from passing through an internal passage of the insertion sheath 116. Therefore, as the vascular puncture closure device 100 is inserted into the insertion sheath 116, the oversized head 120 bears against a proximal surface of a hub portion 117 of insertion sheath 116. Further insertion of the vascular puncture closure device 100 results in sliding movement between the carrier tube 102 and the bypass tube 114, thereby releasing the anchor 108 from the bypass tube 114 (see FIG. 1). Typically, the anchor 108 remains in the flush arrangement shown in FIG. 1 following release from the bypass tube 114, limited in movement by the insertion sheath 116.

The vascular puncture closure device 100 may also include a housing 124 and a pair of sheath connection member 122 that extend distally from the housing 124. The sheath connection members 122 may be constructed to releasably connect the vascular puncture closure device 100 to the insertion sheath 116.

The insertion sheath 116 may include a monofold at a distal end thereof. The monofold acts as a one-way valve to the anchor 108. Typically, monofolds are a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the vascular puncture closure device 100 and the insertion sheath 116 are withdrawn together, ejecting the collagen plug 110 from the carrier tube 102 into the percutaneous incision 119 and exposing the compaction member 112. Further withdrawal of the vascular puncture closure device 100 fully exposes the compaction member 112 as shown in FIG. 4. The operator can then manually compact the collagen plug 110 while cinching together the anchor 108 and collagen plug 110 with the self-tightening slip-knot on the filament 104. Thus, the tissue puncture is sandwiched between the anchor 108 and the collagen plug 110, thereby sealing the vascular puncture 118. The filament 104 is then cut and the percutaneous incision 119 may be closed. The filament 104, anchor 108, and collagen plug 110 are generally made of resorbable materials and therefore remain in place while the vascular puncture 118 heals.

Using the typical vascular puncture closure device 100 described above, however, it may be difficult to eject and compact the collagen plug 110. The insertion sheath 116 resists deformation as the collagen plug 110 is ejected from the carrier tube and compaction may not commence until the insertion sheath 116 has been removed. Under certain conditions, removal of the insertion sheath 116 prior to compacting the collagen plug 110 may cause the collagen plug 110 to retract or displace proximally from the vascular puncture 118, creating an undesirable gap 121 between the collagen plug 110 and the vascular puncture 118. The gap 121 may remain even after compaction, and sometimes results in only a partial seal and bleeding from the vascular puncture 118.

Referring now to FIGS. 5-10B, an example tissue puncture closure device 200 is shown including a compaction assembly, a rotating arm that is selectively operable to drive a compaction member to compact a sealing plug. The tissue puncture closure device 200 includes a carrier tube 202, a suture 204, proximal and distal ends 206, 207, an anchor 208, a sealing plug 210, a compaction assembly 212, and a housing 252. The tissue puncture closure device 200 may be used with a procedural sheath 216 having connectors 215 and a hub 217. Typically, the procedural sheath 216 is inserted into a tissue puncture and the carrier tube 202 is inserted through the procedural sheath 216 to position the anchor 208 within the vessel. Thereafter, the procedural sheath 216 and tissue puncture closure device 200 are interconnected and move concurrently.

Typically, the sealing plug 210 is positioned within the carrier tube 202. The anchor 208 is positioned outside of the carrier tube 202 and at least a portion thereof is positioned between an outer surface of the carrier tube 202 and an inner surface of the procedural sheath 216 when the tissue puncture closure device 200 is inserted through the procedural sheath as shown in at least FIG. 5. The suture 204 is connected to an eye 209 of the anchor 208 and extends through the sealing plug 210 proximally to the compaction assembly 212. When sealing a vessel puncture with the tissue puncture closure device 200, the compaction assembly 212 operates to withdraw the procedural sheath 216 and carrier tube 202 to expose the sealing plug 210 through an outlet 213 of the carrier tube 202 so that the sealing plug 210 is positioned adjacent to a vessel puncture (see FIGS. 7A-8B).

Figure 5:
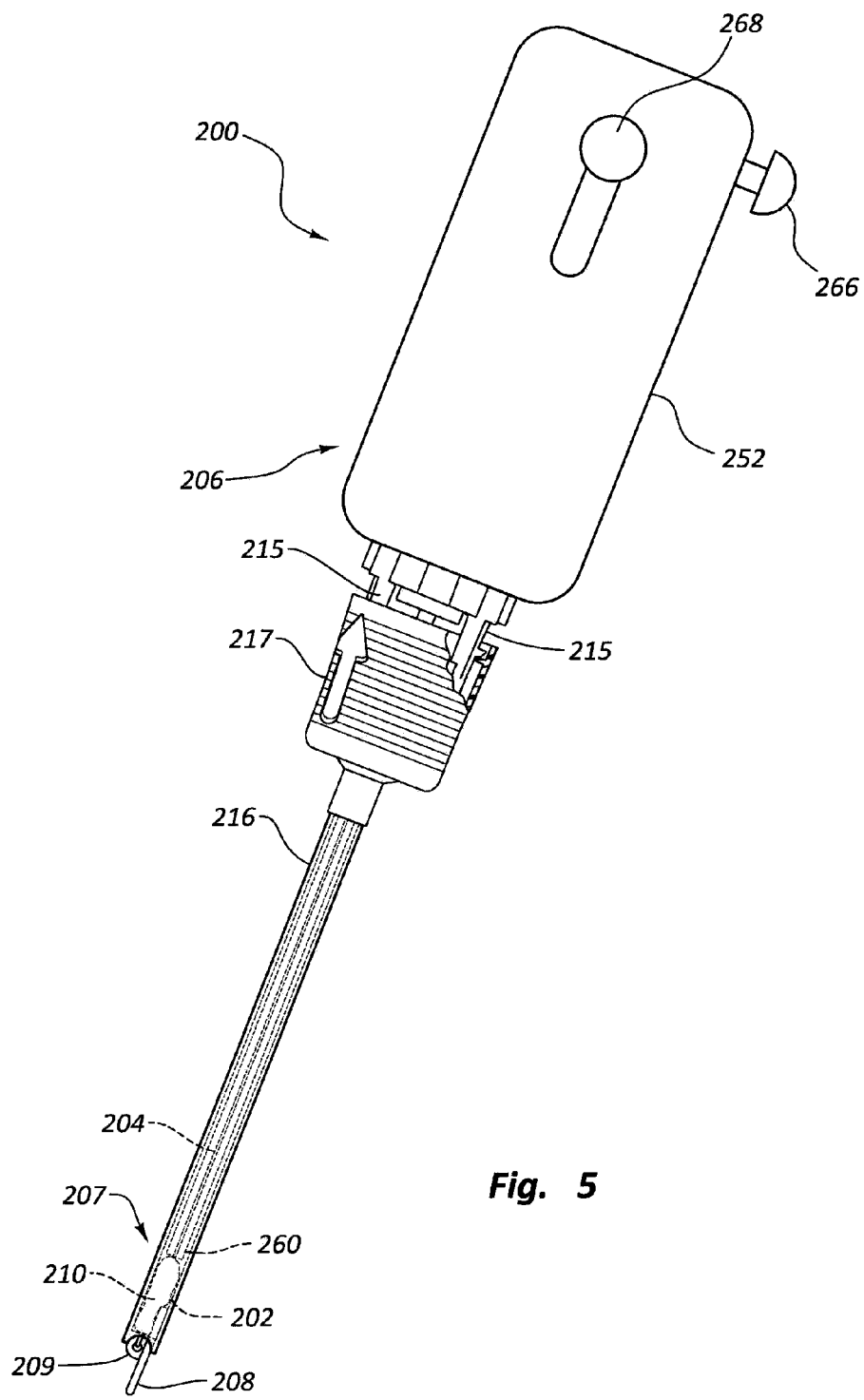
FIG. 5 is a side view of an example tissue puncture closure device in accordance with the present disclosure and inserted into an insertion sheath.
Figure 6:
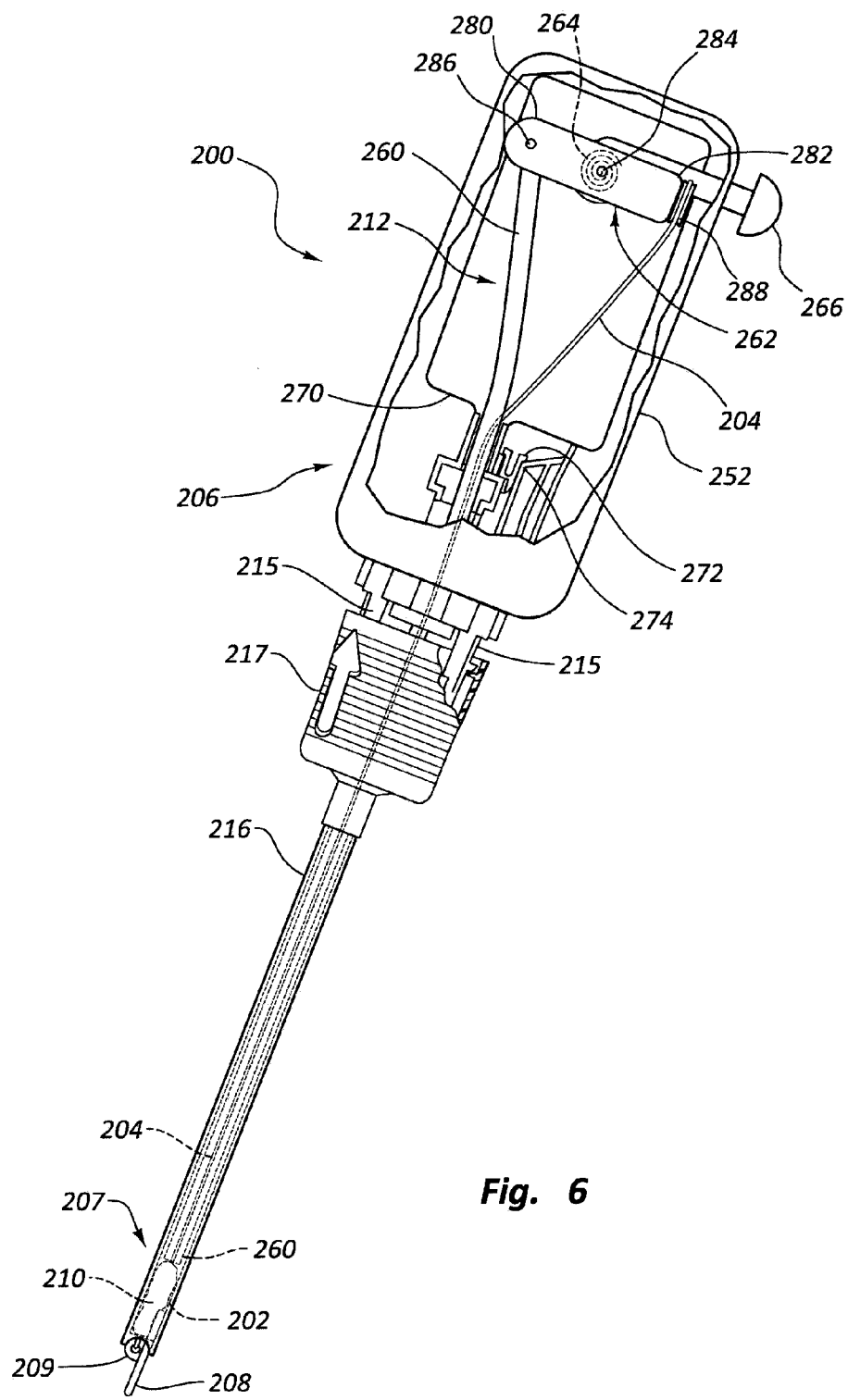
FIG. 6 shows the tissue puncture closure device of FIG. 5 with a housing thereof partially cut away to show a compaction assembly.

Referring to FIG. 6, the compaction assembly 212 includes a compaction tube 260, a pivot member 262, a biasing member 264, a release member 266, a suture release 268 (see FIG. 5), a carriage 270, a stowage detent 272, and a webbing track 274. The compaction tube 260 extends from the housing 252 to the sealing plug 210. The compaction tube 260 may be connected to a pivot member 262. The suture 204 extends from the pivot member 262 to the anchor 208, and may extend through an interior of the compaction tube 260 (e.g., see FIG. 7B).

Figure 10A:
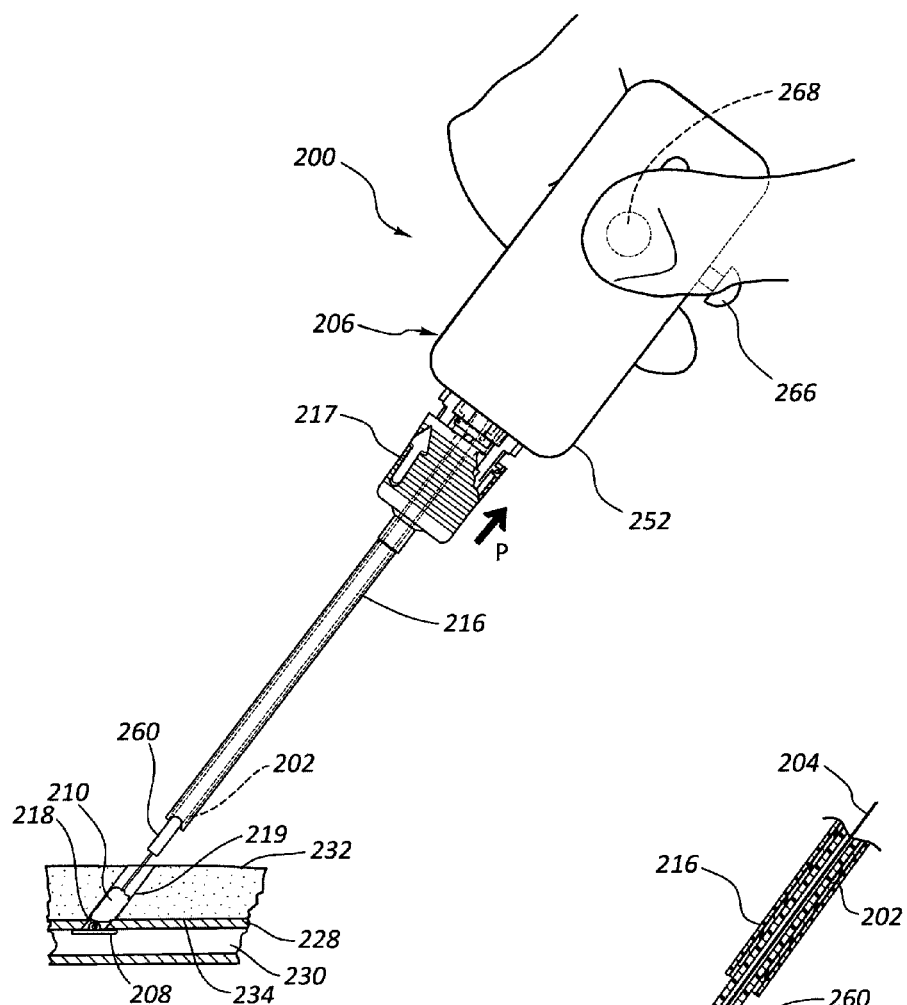
FIG. 10A shows the tissue puncture closure device of FIG. 9A with a suture release member operated to permit withdrawal of the tissue puncture closure device after the sealing plug is compacted.
Figure 10B:
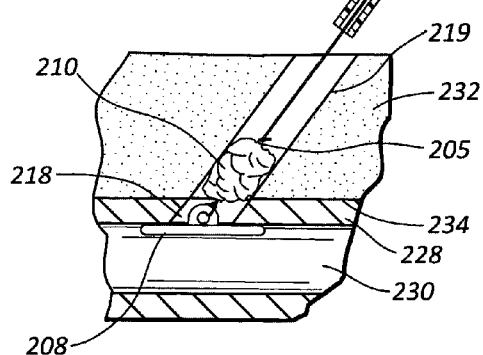
FIG. 10B is a detailed view of a distal end portion of the tissue puncture closure device of FIG. 10A.

The pivot member 262 may include first and second ends 280, 282, a pivot axis or pivot point 284, a tube connection 286, and a pulley 288. The pivot member 262 may be connected to the carriage 270 at a point aligned with the pivot axis 284. The tube connection 286 may provide connection of the compaction tube 260 to the pivot member 262 at the first end 280. The pulley 288 may be connected to the pivot member 262 at the second end 282. The pulley 288 may be configured to rotate relative to the pivot member 262. In some arrangements, the pulley 288 includes a portion of the suture 204 wound thereon. The pulley 288 may be selectively rotatable. For example, the pulley 288 may be maintained in a fixed rotated position during operation of the compaction assembly 212 and until such time as the tissue puncture closure device 200 is released for withdrawal from the tissue puncture as shown in FIGS. 10A and 10B. After the tissue puncture closure device 200 is withdrawn, the suture 204 may be cut, thereby leaving behind the anchor 208 and sealing plug 210 sealing the tissue puncture. In some arrangements, the suture 204 is knotted or tied with a knot 205 (see FIG. 10B) in order to maintain the sealing plug 210 in a compacting state against the anchor 208.

The pivot member 262 may move under a biasing force applied by biasing member 264. Biasing member 264 may be a coil spring or other spring member that applies a biasing force that rotates the pivot member 262 about the pivot axis 284.

Figure 9A:
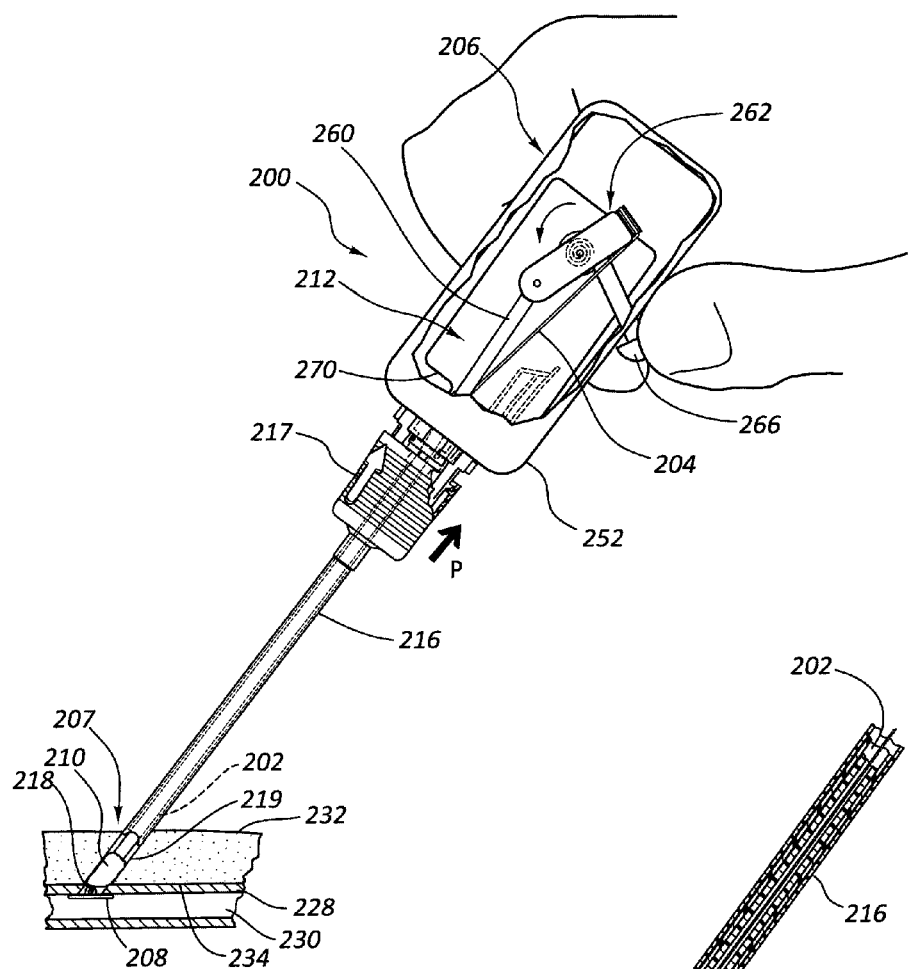
FIG. 9A shows a compaction assembly of the tissue puncture closure device of FIG. 8A operated to compact the sealing plug.

The release member 266 may operate to release the pivot member 262 to rotate from a start position in which the compaction tube 260 is in a withdrawn position (see FIG. 6), to a rotated position in which the compaction tube 260 is advanced to compact the sealing plug 210 (see FIG. 9A). The compaction assembly 212 may include a stop feature (not shown) that holds the pivot member 262 in the initial or start position shown in FIG. 6. The release member 266 may move the stop feature, release the pivot member 262 from contacting the stop member, or in some other way release the pivot member 262 in order to permit rotation of the pivot member 262 under power of the biasing member 264. In other arrangements, the release member 266 holds the biasing member 264 out of contact with the pivot member 262 until the release member 266 is operated. The compaction assembly 212 may include other types of release features that operate in alternative ways to selectively operate the pivot member 262.

The biasing member 264 may apply a constant rotation force to the pivot member 262. In other arrangements, the biasing member 264 may provide an increasing or decreasing rotation force that varies as the pivot member 262 rotates from the initial or start position of FIG. 6 toward the rotated position of FIG. 9A. An increasing rotation force may be helpful in compacting the sealing plug 210, because it may become more difficult to further compact the sealing plug 210 the more the sealing plug 210 is compacted.

The release member 266 may be operable at any location relative to the compaction assembly 212. In one example, the release member 266 is operable along a side edge of the housing 252. The housing 252 may include a slot or channel within which the release member 266 moves as the carriage 270, to which the pivot member 262 is mounted, moves distally within the housing 252.

The suture release 268 (see FIGS. 5 and 10A) may operate to release tension in the suture 204 after the pivot member 262 moves into the rotated position of FIG. 9A to advance the compaction tube 260. The suture release 268 may be aligned with the axis 284 (see FIG. 6) about which the pivot member 262 rotates. The suture release 268 may release tension in the suture 204 in a variety of ways. In one example, the suture release 268 cuts the suture 204 (e.g., within housing 252). In another example, the suture release 268 moves the pivot member 262 to disconnect the biasing member 264 from applying a rotation force to the pivot member 262. In a further example, the suture release 268 operates on the pulley 288 to permit the pulley 288 to rotate, thereby releasing a length of the suture 204. In a still further example, the suture release 268 disconnects the suture 204 from the pulley 288.

The suture release 268 may be accessible along an exterior of the housing 252. In one example, the suture release 268 extends through the housing 252 as shown in FIGS. 5 and 10A. The housing 252 may include a channel or tract within which the suture release 268 freely moves as the carriage 270 moves distally within housing 252.

Carriage 270 is positioned within housing 252. The pivot member 262 may be mounted to the carriage 270. The carriage 270 may be maintained in a proximal position as shown in FIG. 6 until a threshold withdrawal force applied to the housing 252 by an operator is exceeded. The withdrawal force may be applied after the anchor 208 has been positioned within a vessel and the combined tissue puncture closure device 200 and procedural sheath 216 are withdrawn to contact the anchor 208 against an inner surface of the vessel adjacent to the vessel puncture. Further application of the withdrawal force causes the carriage 270 to release within housing 252 and shift distally so that the procedural sheath 216 and carrier tube 202 are withdrawn to expose the sealing plug 210 within a percutaneous incision adjacent to the tissue puncture.

The carriage 270 is maintained in the proximal position of FIG. 6 by contact between a stowage detent 272 and the webbing track 274. The stowage detent 272 may include a flexible arm, which releases from a stop surface of the webbing track 274 after the threshold withdrawal force is exceeded. Typically, the threshold withdrawal force is less than an amount of force needed to pull the anchor 208 through the vessel puncture. For example, the threshold force is less than about 2 lbs. and more preferably less than 1 lb. Other structures and arrangements may be used to releasably hold the carriage 270 within the housing 252. In some examples, a manually-operated release mechanism may be used to release the carriage 270 for distal movement within the housing 252 as opposed to the automatic operation provided by the stowage detent 272 and webbing track 274.

Figure 7A:
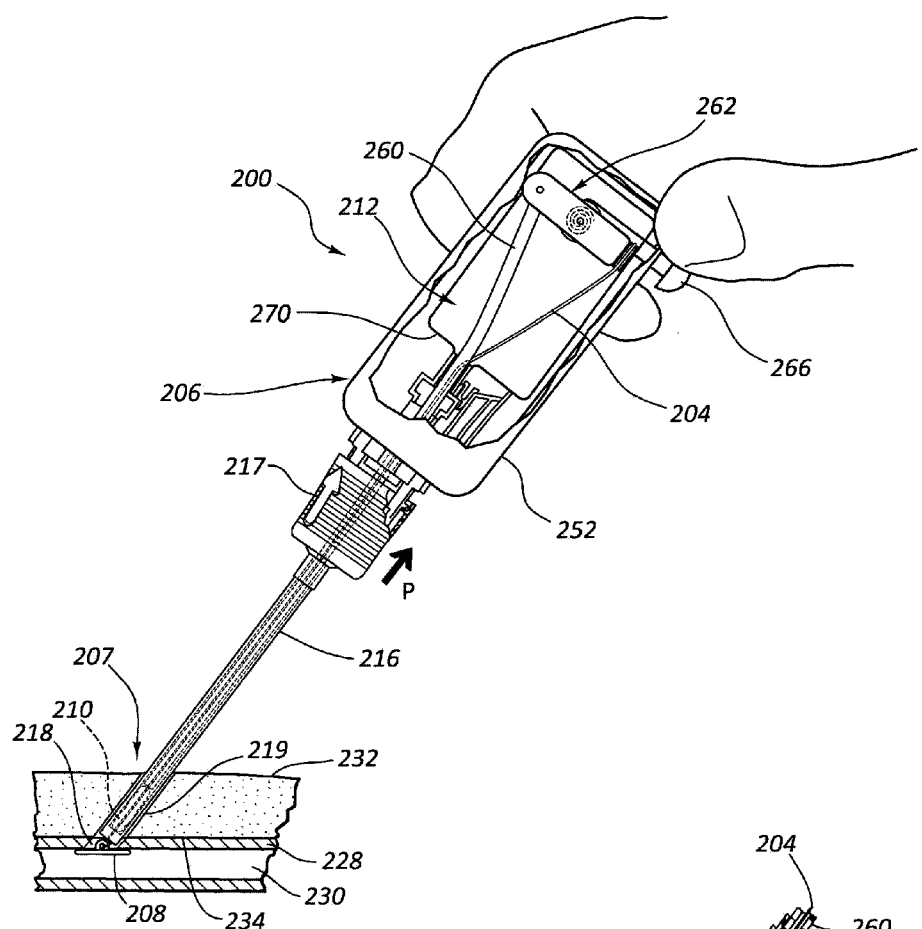
FIG. 7A shows the tissue puncture closure device of FIG. 6 inserted through a tissue puncture and into a vessel interior.

Referring now to FIGS. 7A-10B, an example method of sealing a vessel puncture using the tissue puncture closure device 200 and procedural sheath 216 is described in further detail. FIG. 7A shows the procedural sheath 216 advanced through a percutaneous incision 219 of a tissue layer 232 and at least partially into a vessel puncture 218 in a vessel wall 234 of a vessel 228. The carrier tube 202 of the tissue puncture closure device 200 is advanced through the hub 217 of the procedural sheath 216 until the anchor 208 protrudes beyond a distal open end of the procedural sheath 216 within a lumen 230 of the vessel 228. The anchor 208 rotates into a position in which the anchor 208 contacts an inner surface of the vessel 228. The operator may apply a withdrawal force to the housing 252 to draw the anchor 208 into contact with the inner surface of the vessel 228.

Figure 7B:
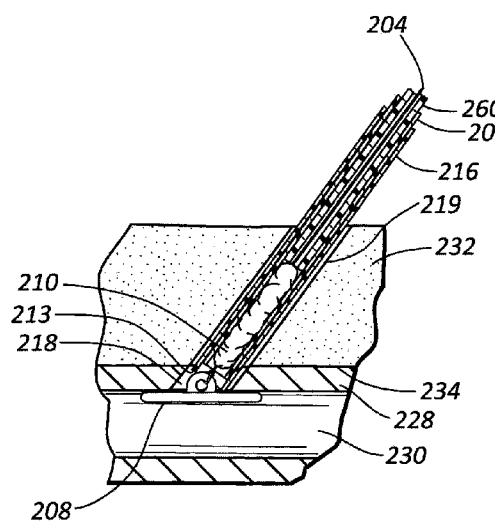
FIG. 7B is a detailed view of a distal end portion of the tissue puncture closure device of FIG. 7A.

FIG. 7B shows a close-up view of the tissue puncture closure device 200 and procedural sheath 216 relative to the vessel 228 and tissue layer 232. The compaction tube 260 is shown positioned directly proximal of and in contact with the sealing plug 210. The compaction tube 260 may provide a backstop (e.g., stop surface) that maintains the sealing plug 210 in a fixed axial position during further operation of the tissue puncture closure device 200 as described with reference to the following figures.

Figure 8A:
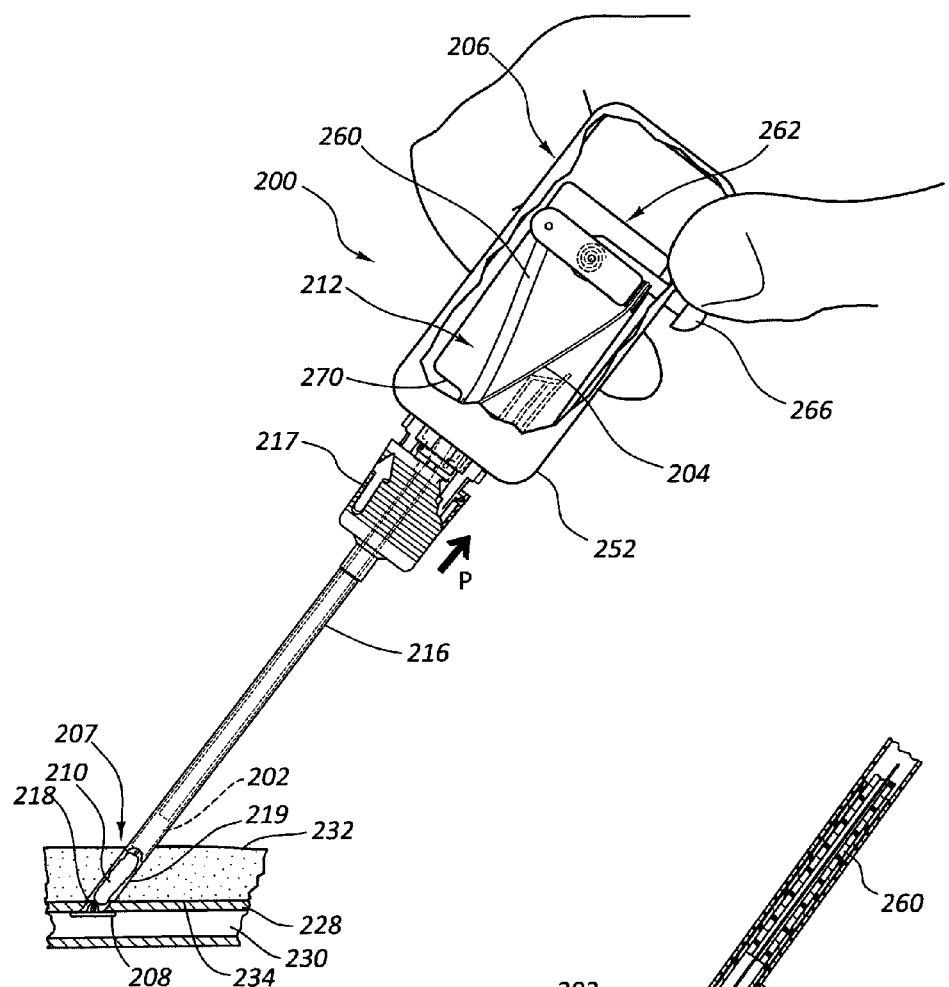
FIG. 8A is a side view of the tissue puncture closure device of FIG. 7A withdrawn to remove the insertion sheath and a carrier tube to expose a sealing plug within the tissue puncture.

Referring now to FIG. 8A, applying a further withdrawal force in the direction P in an amount that exceeds a threshold withdrawal force causes the stowage detent 272 to release from the stop surface of the webbing track 274 so that the carriage 270 shifts distally within the housing 252. The pivot member 262 maintains the initial or starting rotated position shown in FIGS. 7A and 8A as the carriage 270 shifts distally. Described in another way, the carriage 270 maintains a fixed axial position and the housing 252 shifts proximally as the operator applies a withdrawal force in the direction P shown in FIG. 8A so that the procedural sheath 216 and carrier tube 202 are withdrawn to expose the sealing plug 210 within the percutaneous incision 219.

Figure 8B:
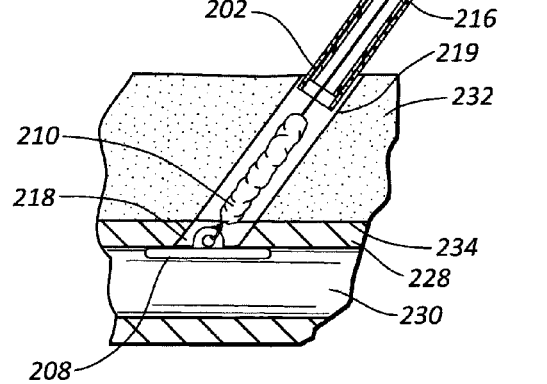
FIG. 8B is a detailed view of a distal end portion of the tissue puncture device of FIG. 8A.

FIG. 8B is a close-up view of a distal end portion of the tissue puncture closure device 200 and procedural sheath 216 showing withdrawal of the procedural sheath 216 and carrier tube 202 to expose the sealing plug 210.

FIG. 9A shows the operator actuating the release member 266 to permit rotation of the pivot member 262. The pivot member 262 rotates counterclockwise to apply tension in the suture 204 and concurrently advance the compaction tube 260. Advancing the compaction tube 260 provides compaction of the sealing plug 210 within the percutaneous incision 219. The compacted sealing plug 210 may be compacted against an outer surface of the vessel 228 adjacent to the vessel puncture 218 to seal vessel puncture 218. Tension in the suture 204 may firmly hold the anchor 208 against an inner surface of the vessel 228 to provide a backstop against which the sealing plug 210 is compacted by the compaction tube 260.

Figure 9B:
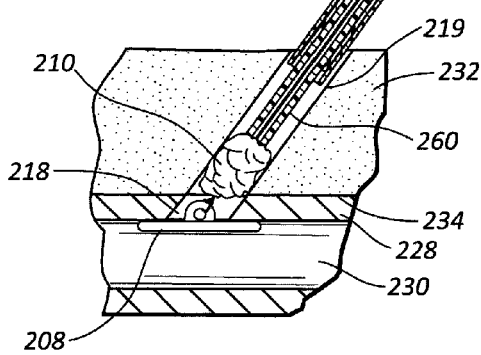
FIG. 9B is a detailed view of a distal end portion of the tissue puncture closure device of FIG. 9A.

FIG. 9B is a close-up view of a distal end portion of the tissue puncture closure device 200 of FIG. 9A showing compaction of sealing plug 210 and sealing of the vessel puncture 218.

The compaction assembly 212 may be referred to as a "push/pull" compaction system because the compaction assembly 212 provide a push force and a pull force to compact the sealing plug 210. The push force is applied to the compaction tube 260 and the pull force is applied to the suture 204. The push force may be applied to a proximal end of the compaction tube 260, and the pull force may be applied to a proximal end of the suture 204.

The suture 204 may be connected to the pivot member 262 at a distance from pivot axis 284 that is substantially the same as the distance between the tube connection 286 of the compaction tube 260 to the pivot member 262. This equidistant connection of the suture 204 and compaction tube 260 to the pivot member 262 may result in a 1:1 ratio for longitudinal movement of the suture 204 and compaction tube 260 as the pivot member 262 rotates.

Connecting the suture 204 and compaction tube 260 at other locations (i.e., at non-equidistant points) on the pivot member 262 may result in different ratios of movement for the suture 204 and compaction tube 260 in a longitudinal direction (i.e., relative to a length dimension of the tissue puncture closure device 200). Different ratios may be desirable if, for example, the operator wishes to apply less force between anchor 208 and the vessel 228 as compared to the amount of compaction force required for compacting the sealing plug 210, or an opposite result. Typically, the ratios are in the range of about 0.25:1 to about 4:1 for movement of the suture 204 relative to movement of the compaction tube 260.

After the sealing plug 210 is compacted and the vessel puncture 218 is sealed, the operator may operate the suture release 268 to release tension in suture 204 as shown in FIG. 10A. The reduced tension in suture 204 may permit the operator to withdraw the tissue puncture closure device 200 away from the tissue layer 232. Withdrawing the tissue puncture closure device 200 may expose the suture 204. The operator may then use a cutting device to cut suture 204. FIG. 10B shows the tissue puncture closure device 200 withdrawn and the suture 204 exposed for cutting. The suture 204 may be cut below an outer surface of the tissue layer 232. Any desired cutting means may be used to cut the suture 204. Prior to cutting suture 204, the operator may tie the knot 205 (see FIG. 10B) in suture 204 and slide the knot into contact with the sealing plug 210. The knot 205 may assist in maintaining the sealing plug 210 in the compacted position of FIGS. 10A and 10B. The knot 205 may be a slip-knot that tightens as the suture 204 is tensioned. The knot 205 may automatically tighten and maintain tension in the suture 204.

The pivot member 262 is shown in the drawings as a generally elongate structure having a greater length than width. Many other shapes and sizes are possible for pivot member 262. In some examples, the pivot member 262 may have a rectangular, triangular, or oval shape. Other features and functions of the tissue puncture closure device 200 may vary in other embodiments. For example, the housing 252 may have any desired shape and size to accommodate the compaction assembly 212. The compaction assembly 212 may include additional or fewer features than those shown in the figures. In one example, the compaction assembly 212 may include a separate compaction member that contacts the sealing plug 210 and is advanced by a compaction member that is attached to the pivot member 262.

The example tissue puncture closure device 200 shown with reference to FIGS. 5-10B includes manually actuated features for operating the pivot member 262. Other embodiments may include an automatically operable pivot member. For example, the pivot member may be automatically released for rotation after exceeding a threshold withdrawal force. Typically, the threshold withdrawal force for operating the pivot member would be greater than the threshold force for releasing the stowage detent 272 that controls movement of the carriage 270 so that the carriage 270 is released within the housing before the pivot member 262 rotates.

As used in this specification and the appended claims, the term "compact," "compacting," or "compaction" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The term "effecting" means producing an outcome, achieving a result, or bringing about. The words "including" and "having," as used in the specification, including the claims, have the same meaning as the word "comprising."

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device, comprising:
   an anchor;
   a suture connected to the anchor at a distal end of the suture;
   a sealing plug slidingly mounted to the suture and positioned proximal of the anchor;
   a compaction assembly, comprising:

a compaction tube having a distal end and a proximal end;

a pivot arm having first and second ends and being rotatable about a pivot axis, the proximal end of the compaction tube being connected to the first end of the pivot arm and a proximal end of the suture being connected to the second end of the pivot arm;

a release member operable to release the pivot arm to rotate between a first position wherein the compaction tube is withdrawn, and a second position wherein the pivot arm pulls the suture to apply tension in the suture and the pivot arm pushes the compaction tube to compact the sealing plug.

2. The tissue puncture closure device of claim 1, wherein the compaction assembly provides a 1:1 ratio of longitudinal movement of the compaction tube and suture when the pivot arm rotates.

3. The tissue puncture closure device of claim 1, wherein the compaction assembly comprises a biasing member operable to bias the pivot arm toward the second position.

4. The tissue puncture closure device of claim 1, further comprising a housing, the pivot arm being positioned in the housing.

5. The tissue puncture closure device of claim 4, wherein the compaction assembly is slidable in a distal direction relative to the housing.

6. The tissue puncture closure device of claim 1, further comprising a carrier tube, the sealing plug being positioned in the carrier tube during insertion of the tissue puncture closure device into a puncture.

7. The tissue puncture closure device of claim 6, wherein the carrier tube retracts relative to the sealing plug to expose the sealing plug at a location adjacent to the puncture.

8. The tissue puncture closure device of claim 1, wherein the pivot axis is arranged perpendicular to a direction of motion of the compaction tube.

9. The tissue puncture closure device of claim 1, further comprising a suture release operable to release tension in the suture after the sealing plug is compacted by the compaction tube.

10. The tissue puncture closure device of claim 1, wherein the compaction assembly comprises a spool mounted to the second end of the pivot arm, the suture being wound about the spool.

11. The tissue puncture closure device of claim 1, wherein the release member is manually operated upon withdrawal of the tissue puncture closure device from a tissue puncture.

12. A tissue puncture closure device adapted for insertion into and sealing of a tissue puncture, the tissue puncture closure device comprising:
   a carrier tube;
   a sealing plug;
   an anchor;
   a suture connected to the anchor and extending through the carrier tube;
   a compaction member;
   a pivot member having first and second end portions, the compaction member being coupled to the first end portion and the suture being coupled to the second end portion;
   wherein responsive to rotating the pivot member, the pivot member pulls the suture to apply tension in the suture and the pivot member pushes and advances the compaction member to compact the sealing plug toward the anchor.

13. The tissue puncture closure device of claim 12, wherein the compaction member and suture are coupled to the pivot member at locations equidistant from a rotation axis about which the pivot member rotates.

14. The tissue puncture closure device of claim 12, wherein the pivot member has a rotation axis that is arranged perpendicular to a length dimension of the tissue puncture closure device.

15. The tissue puncture closure device of claim 12, wherein pivoting the pivot member moves the compaction member between a withdrawn position and an advanced position.

16. The tissue puncture closure device of claim 12, wherein the suture and compaction member are attached to opposite ends of the pivot member.

17. A method of sealing a puncture in a wall of a vessel, the method comprising:
   providing a closure device having a sealing plug, an anchor, a compaction member, a suture connected to the anchor, and a pivot member, the pivot member being connected to the suture and connected to the compaction member, wherein the compaction member is coupled to a first end portion of the pivot member and the suture is coupled to a second end portion of the pivot member;
   inserting the closure device through the puncture to position the anchor within an interior of the vessel;
   withdrawing the closure device to contact the anchor against an interior surface of the vessel and deposit the sealing plug adjacent to an exterior surface of the vessel;
   rotating the pivot member, wherein the pivot member pulls the suture and applies tension in the suture and the pivot member pushes the compaction member to compact the sealing plug to seal the puncture.

18. The method of claim 17, wherein rotating the pivot member includes rotating the pivot member about a pivot axis.

19. The method of claim 17, further comprising providing a carrier tube configured to house the sealing plug when inserting the closure device through the puncture, and ejecting the sealing plug from the carrier tube occurs before rotating the pivot member.

20. The method of claim 17, further comprising providing a housing, the pivot member being positioned in the housing, and shifting the pivot member distally within the housing prior to rotating the pivot member.

* * * * *